(12) United States Patent
Lyons et al.

(10) Patent No.: US 11,737,817 B2
(45) Date of Patent: Aug. 29, 2023

(54) METHODS AND SYSTEMS FOR CONTROLLING ENERGY DELIVERY IN MEDICAL DEVICES

(71) Applicant: Boston Scientific Scimed, Inc., Maple Grove, MN (US)

(72) Inventors: Gerald Lyons, Saratoga, CA (US); Amr Salahieh, Saratoga, CA (US); Daniel Lundberg, Campbell, CA (US); Ron Avisa, Newark, CA (US); Guy McNally, Los Altos, CA (US); Rodica Schileru, San Jose, CA (US); Thomas Breton, San Jose, CA (US); Adnan Merchant, Fremont, CA (US); John P. Claude, Redwood City, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 761 days.

(21) Appl. No.: 16/094,721

(22) PCT Filed: Apr. 18, 2017

(86) PCT No.: PCT/US2017/028174
§ 371 (c)(1),
(2) Date: Oct. 18, 2018

(87) PCT Pub. No.: WO2017/184628
PCT Pub. Date: Oct. 26, 2017

(65) Prior Publication Data
US 2021/0228269 A1    Jul. 29, 2021

Related U.S. Application Data

(60) Provisional application No. 62/484,378, filed on Apr. 11, 2017, provisional application No. 62/324,175, filed on Apr. 18, 2016.

(51) Int. Cl.
A61B 18/14    (2006.01)
A61B 18/12    (2006.01)
A61B 18/00    (2006.01)

(52) U.S. Cl.
CPC ...... *A61B 18/1492* (2013.01); *A61B 18/1206* (2013.01); *A61B 2018/0072* (2013.01);
(Continued)

(58) Field of Classification Search
CPC ............ A61B 18/1492; A61B 18/1206; A61B 2018/00577; A61B 2018/00755; A61B 2560/0487; A61B 2018/126
See application file for complete search history.

(56) References Cited

U.S. PATENT DOCUMENTS 6,014,581 A *  1/2000  Whayne ............... A61B 5/6858
                                          600/523
6,358,245 B1 * 3/2002  Edwards ............ A61B 18/1206
                                          606/42

(Continued)

FOREIGN PATENT DOCUMENTS

CN    102525642 A    7/2012
CN    102895028 A    1/2013

(Continued)

OTHER PUBLICATIONS

Partial Supplementary European Search Report issued in EP17786483.2, dated Nov. 29, 2019, 10 pages.

(Continued)

*Primary Examiner* — Ronald Hupczey, Jr.
(74) *Attorney, Agent, or Firm* — Nelson Mullins Riley & Scarborough (57) ABSTRACT

Systems for controlling ablation procedures that include a user interface. The user interface can include a display; and a memory with a computer executable method stored
(Continued)

thereon, the computer executable method adapted to cause to be displayed on the display a plurality of interactive elements for controlling one or more aspects of the ablation.

15 Claims, 5 Drawing Sheets

(52) U.S. Cl.
CPC ............... *A61B 2018/00351* (2013.01); *A61B 2018/00577* (2013.01); *A61B 2018/00672* (2013.01); *A61B 2018/00755* (2013.01); *A61B 2018/00767* (2013.01); *A61B 2018/126* (2013.01); *A61B 2560/0487* (2013.01)

(56) References Cited

U.S. PATENT DOCUMENTS

| | | | |
|---|---|---|---|
| 9,174,052 B1* | 11/2015 | Nabutovsky | A61N 1/36071 |
| 9,333,031 B2 | 5/2016 | Salahieh et al. | |
| 2003/0216733 A1 | 11/2003 | McClurken et al. | |
| 2006/0271040 A1* | 11/2006 | Horne | A61M 25/10 |
| | | | 606/49 |
| 2008/0228182 A1* | 9/2008 | Young | A61B 18/1477 |
| | | | 606/41 |
| 2009/0149917 A1 | 6/2009 | Whitehurst et al. | |
| 2010/0049031 A1 | 2/2010 | Fruland et al. | |
| 2011/0288539 A1* | 11/2011 | Woloszko | A61B 18/1206 |
| | | | 606/33 |
| 2012/0059367 A1 | 3/2012 | Buysse et al. | |
| 2012/0116386 A1* | 5/2012 | Govari | A61B 18/1492 |
| | | | 606/41 |
| 2012/0300953 A1* | 11/2012 | Mauch | H04R 25/554 |
| | | | 381/60 |
| 2014/0171942 A1 | 6/2014 | Werneth et al. | |
| 2014/0257269 A1 | 9/2014 | Woloszko et al. | |
| 2015/0320481 A1* | 11/2015 | Cosman, Jr. | A61B 34/10 |
| | | | 606/35 |
| 2015/0351836 A1 | 12/2015 | Prutchi | |
| 2017/0042614 A1* | 2/2017 | Salahieh | A61B 18/1206 |
| 2017/0065340 A1* | 3/2017 | Long | A61B 18/1492 |

FOREIGN PATENT DOCUMENTS

| | | | | |
|---|---|---|---|---|
| CN | 103718571 A | * | 4/2014 | ........... A61N 1/0541 |
| CN | 105209111 A | | 12/2015 | |
| EP | 1169976 A1 | | 1/2002 | |
| JP | 2005-525861 | | 9/2005 | |
| JP | 2015-083132 A | | 4/2015 | |
| JP | 2019-513532 A | | 5/2019 | |
| JP | 6648337 B2 | | 2/2020 | |
| WO | 2015/148470 A1 | | 10/2015 | |
| WO | 2015/175944 A1 | | 11/2015 | |
| WO | 2017087549 A1 | | 5/2017 | |
| WO | 2017/184628 A1 | | 12/2017 | |

OTHER PUBLICATIONS

International Preliminary Report on Patentability issued in PCT/US2017/028174, dated Nov. 1, 2018, 9 pages.
International Search Report and Written Opinion issued in PCT/US2017/028174, dated Jun. 29, 2017, 10 pages.

* cited by examiner

METHODS AND SYSTEMS FOR CONTROLLING ENERGY DELIVERY IN MEDICAL DEVICES

CROSS-REFERENCE TO RELATED APPLICATIONS

This application is a national phase application of PCT Application No. PCT/US2017/028174, internationally filed Apr. 18, 2017, which claims priority to the following U.S. Provisional Patent Applications: 62/324,175, filed Apr. 18, 2016; and 62/484,378, filed Apr. 11, 2017, all of which are incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Improved methods and systems are needed for controlling one or more aspects of energy delivery systems, optionally ablation systems.

SUMMARY OF THE DISCLOSURE

One aspect of the disclosure is a system for controlling an ablation procedure, comprising: a user interface comprising a display; and a memory with a computer executable method stored thereon, the computer executable method adapted to cause to be displayed on the display a plurality of graphical elements, each of the plurality of graphical elements representing a corresponding electrode carried by an ablation catheter in communication with an ablation energy generator, the computer executable method further adapted to, in response to user interaction with the display in a manner specific to one of the plurality of graphical elements, toggle the respective plurality of graphical elements between at least an active source state having an active source visual indicator, an active sink state having an active sink visual indicator, and an inactive state with an inactive state visual indicator, wherein each of the three visual indicators are unique, wherein the active source state designates to the system that the respective electrode is one of a plurality of active source electrodes, wherein the active sink state designates to the system that the respective electrode is one of a plurality of active sink electrodes, wherein the plurality of active source electrodes together create a first pole in a bipolar mode, and wherein the plurality of active sink electrodes together create a second pole in the bipolar mode, wherein the system is adapted to connect the plurality of active sink electrodes to a ground, and to connect the plurality of active source electrodes to a source.

In some embodiments, if the number of active source electrodes in the plurality of active source electrodes is equal to the number of active sink electrodes in the plurality of active sink electrodes, delivery of the ablation energy comprises dividing substantially equally an energy output between the set of active source electrodes and the set of active sink electrodes.

In some embodiments, the energy density at each of the active electrodes is substantially equivalent. The energy density at each of the plurality of active sink electrodes can be no more than 20% less than the energy density at each of the plurality of sources, and optionally 10% less. The difference in energy densities can be due to a difference in the number of active sink electrodes and the active source electrodes.

In some embodiments, the computer executable method is further adapted to, in response to user interaction with the display in a manner specific to one of the plurality of graphical elements, also toggle the respective plurality of graphical elements between a selected state with a selected state visual indicator, wherein the selected state visual indicator is different than the active source visual indicator, the active sink visual indicator, and the inactive state visual indicator.

One aspect of the disclosure is a method of controlling an ablation procedure, comprising: displaying on a user interface display a plurality of graphical elements, each of the plurality of graphical elements representing a corresponding electrode carried by an ablation catheter in communication with an ablation energy generator, and in response to user interaction with the display in a manner specific to one of the plurality of graphical elements, toggling the respective plurality of graphical elements between at least an active source state having an active source visual indicator, an active sink state having an active sink visual indicator, and an inactive state with an inactive state visual indicator, wherein each of the three visual indicators are unique; designating any electrode with an active source state as one of a plurality of active source electrodes; designating any electrode with an active sink state as one of a plurality of active sink electrodes; designating the plurality of active source electrodes together as a first pole in a bipolar mode, and designating the plurality of active sink electrodes together as a second pole in the bipolar mode; and connecting the plurality of active sink electrodes to a ground, and connecting the plurality of active source electrodes to a source.

In some embodiments, the method further comprises delivering ablation energy from the energy generator to the first pole.

In some embodiments, the method further comprises stopping energy delivery to any electrode if a monitored change in impedance indicates an abrupt and significant change in calculated impedance.

In some embodiments, the method further comprises stopping energy delivery to any electrode if a monitored impedance reaches a minimum threshold impedance and/or a maximum impedance threshold (optionally a relative impedance), which can occur automatically or via user input.

One aspect of the disclosure is a system for monitoring an ablation procedure, comprising: an ablation catheter including a plurality of ablation electrodes; an energy generator in communication with the ablation electrodes; the system adapted to designate a subset of the ablation electrodes as sources and to designate a subset of the ablation electrodes as sinks; a computer executable method adapted to calculate impedance associated with each of the sources and each of the sinks and tissue adjacent the respective source or sink based on a voltage and current delivered from the energy generator, wherein the impedance at the sources is calculated in a first manner, and the impedance at the sinks is calculated in a second manner different than the first manner.

In some embodiments, the computer executable method is adapted to calculate the sink impedances as a percentage of the calculated source impedances.

In some embodiments, the method further comprises a user interface comprising a display, the display including a plurality of impedance history regions, each one of the plurality of impedance history regions designated for one of the plurality of ablation electrodes, the system adapted to display on each of the plurality of impedance history regions the respective calculated impedances over time to thereby create a plurality of impedance histories, one for each of the selected plurality of ablation electrodes. The system can be adapted to visually indicate on each of the plurality of time histories if the respective impedance drops below a threshold impedance, which can optionally be a relative threshold impedance.

In some embodiments, the method is further adapted to cease energy delivery to any of the plurality of ablation electrodes if the impedance for any of the plurality of electrodes increases or decreases abruptly. The system can be adapted to visually indicate on any of the impedance histories if energy delivery has ceased for any of the respective ablation electrodes.

DETAILED DESCRIPTION

The disclosure relates to systems and methods for controlling the use of energy delivery devices, such as cardiac ablation devices. The disclosure includes user interfaces, and methods of using the interfaces, that facilitate controlling energy delivery to the energy delivery devices. The disclosure also includes methods such as algorithms, and devices on which they are stored, that facilitate the control of energy delivered to the energy delivery devices.

The disclosure herein describes systems and methods in the context of an exemplary energy delivery device, and in particular an exemplary ablation device, but it is understood that the concepts herein may be applicable to many other types of energy delivery devices, including other tissue ablation devices. The exemplary energy delivery devices herein can be used within the heart for treatment of, for example, fibrillation, atrial fibrillation, or ventricular fibrillation.

Figure 1:
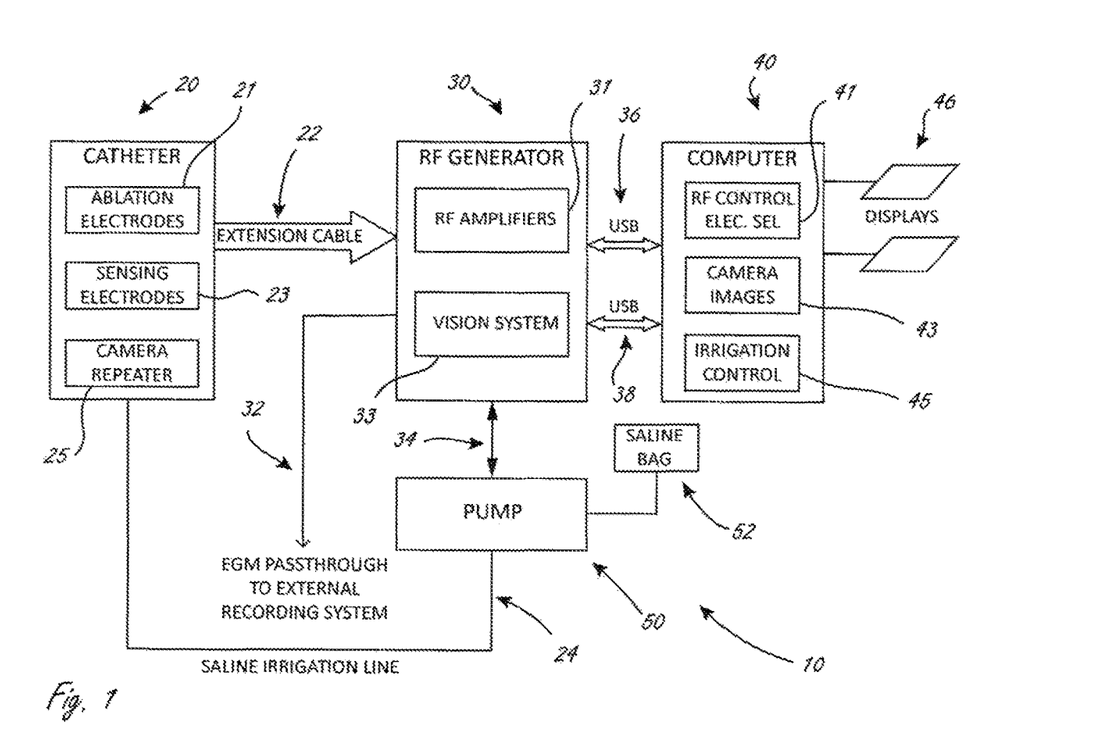
FIG. 1 is an exemplary system that can include the methods and devices herein.

FIG. 1 shows an exemplary system for controlling the delivery of ablation energy to an exemplary energy delivery device. Energy delivery device, as used herein, refers to the device that is positioned proximate tissue and applies the energy to tissue (see FIG. 2, for example). An energy "generator" refers to a device that generates energy, and is generally disposed outside the patient, and is in operable communication with the energy delivery device. System 10 includes catheter 20 coupled to RF generator 30 via connection 22, and computer 40 in communication with RF generator 30 via connections 36 and 38 (e.g., USB or any other type). System 10 also includes one or more displays 46 in communication with computer 40. System 10 also includes pump 50 and fluid source 52, wherein the pump 50 is adapted to pump fluid from fluid source 52 to catheter 20. Pump is in communication with catheter 20 and RF generator via two-way connection 34. RF generator 30 includes electrogram signal (EGM) passthrough 32 to an external recording system. Catheter 20 includes ablation electrodes 21, sensing electrodes 23, and optics 25. RF generator 30 includes RF amplifier 31 and vision system 33. Computer 40 includes RF control and electrode selection 41, camera imager 43, and irrigation control 45.

Figure 2:
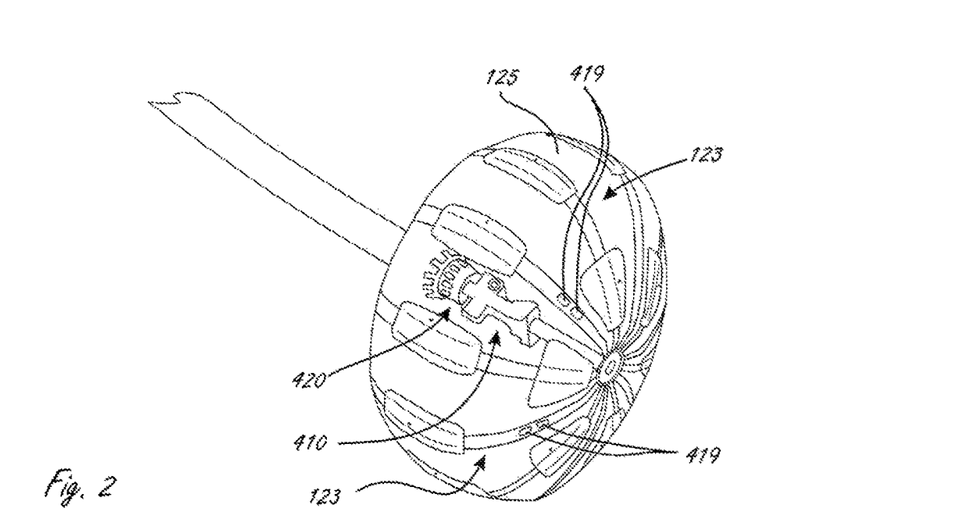
FIG. 2 is a distal region of an exemplary energy delivery device.

FIG. 2 illustrates a distal working end of an exemplary energy delivery device, and in this embodiment is a tissue ablation device. More details of the tissue ablation device shown in FIG. 2, and other similar tissue ablation devices, including their methods of use, can be found in PCT/US 16/62323, titled "Energy delivery devices," filed Nov. 16, 2016; and U.S. Pat. No. 9,333,031, issued May 10, 2016, both of which are incorporated by reference herein.

The energy delivery device in FIG. 2 includes an optional inflatable member (e.g., balloon) and a plurality of electrodes carried by (directly or indirectly) the inflatable member. In alternative embodiments, the electrodes could be carried on splines or other deformable elements, and an inflatable member need not be part of the energy delivery device.

The energy delivery device includes a plurality of electrodes, and in this embodiment it is eighteen electrodes. More or fewer electrodes can be used in alternative embodiments. The plurality of electrodes includes a set of proximal electrodes and a set of distal electrodes. As described in more detail in PCT/US 16/62323 and U.S. Pat. No. 9,333,031, energy is delivered to one or more electrodes (e.g., in bipolar or monopolar mode) and then into tissue that is proximate the electrodes. The systems and methods herein are adapted to and are used to abate tissue proximate the one or more electrodes.

The ablation devices described in FIG. 2 and in PCT/US 16/62323 and U.S. Pat. No. 9,333,031 include an optional optical system within the inflatable member that is adapted to provide visualization of tissue when the inflatable member is inflated and the inflatable member is advanced against tissue. Details of exemplary optical systems (e.g., cameras and light sources) can be found in PCT/US 16/62323 and U.S. Pat. No. 9,333,031.

Figure 3:
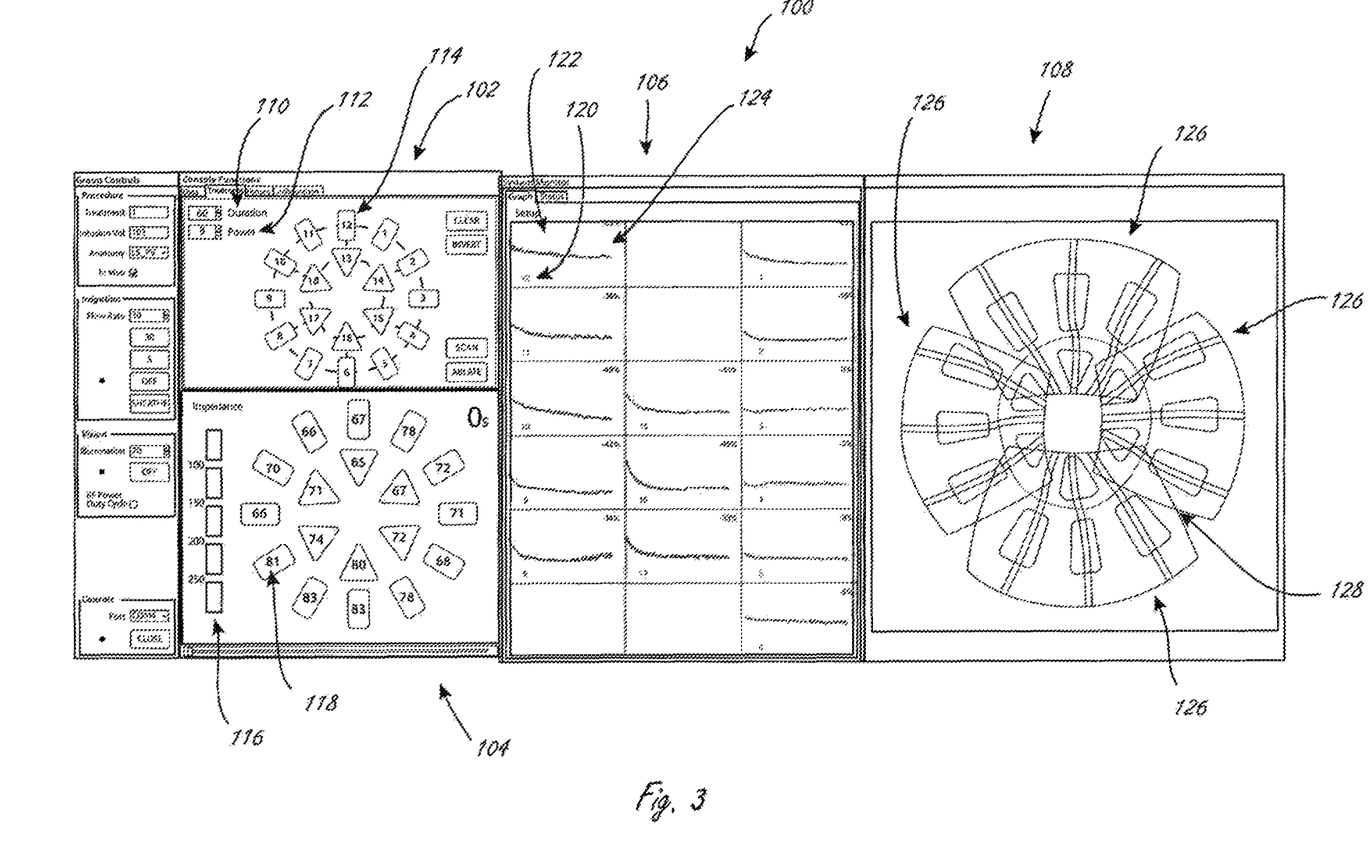
FIG. 3 is an exemplary user interface.

FIG. 3 illustrates an exemplary user interface that is displayed on a monitor (e.g., a computer monitor) and allows for a user (e.g., physician) to interact with the overall system. The user interface includes a plurality of sections, or regions, that are shown presented in different windows. It is understood that any of the interface visual elements can be grouped differently than is shown in FIG. 3 without departing from the scope of the disclosure. For example, sections or regions that are shown in different windows in FIG. 3 could be grouped into a single window.

The user interface in FIG. 3 includes a first section 102 that includes that includes a top section and a bottom section, which represent different but related information. The top section includes a plurality of graphical elements 114, each of which visually represents one of the electrodes on the energy delivery device. Graphical elements 114 are presented in 2D, and represent the configuration of the electrodes on the energy delivery device if those electrodes were translated into a flat 2D space. The graphical elements includes an outer ring of graphical elements, which represent the proximal ring of electrodes on the energy delivery device, and an inner ring of graphical elements, which represent the distal (relative to the proximal electrodes) ring of electrodes on the energy delivery device. The graphical elements 114 have shapes that correspond to the shapes of the electrodes. The graphical elements 114 also have an alphanumeric identifier associated therewith for easy identification. In this embodiment the graphical elements are numbers 1-18 to correspond with the eighteen electrodes on the energy delivery device.

The top section also includes a power interface 112, which is adapted to allow a user to select a power for the energy to be delivered. The top section also includes a duration interface 110, which allows a user to select a duration of the energy delivery. In embodiments herein, the system can be adapted such that each of the source electrodes (described herein) can be set with its own power setting, and its own duration.

The system is adapted with software such that each of the graphical elements 114 is selectable by a user. When a user interacts with the user interface in some way (e.g., touching a touch screen, using an input device like a mouse to select), this is considered to be a user "event," which can trigger some action dictated by one or more algorithms controlling the interface and the user interacting with the interface.

The interface also includes impedance history section 106 and visualization section 108, which are described in more detail below.

The disclosure will now describe exemplary uses of the energy delivery device, and how the user interface facilitates such uses. The exemplary uses will further describe the other sections of the user interface shown in FIG. 3. Not all method steps described below need be carried out, and some are merely exemplary and described in the context of the exemplary energy delivery device described herein. To prepare for an ablation procedure, the inflatable member can be inflated with fluid outside of the patient, to force air bubbles out of the irrigation holes in the irrigation member. In some embodiments the balloon is inflated with saline in an ultrasonic bath, which helps to breakup bubbles and thereby there removal through the irrigation holes. This will prevent air bubbles from being delivered into the patient from the inflatable member after the device is advanced into the patient and inflation fluid is delivered into the inflation member to inflate the inflatable member. It additionally prevents air bubbles from masking portions of the image captured by the imaging system. The energy delivery system is then deflated and introduced into a delivery catheter for advancement into the patient.

After the energy delivery device has been advanced through the patient and is positioned proximate target tissue in the patient (e.g., in a left atrium proximate to left atrial tissue), the optional visualization system can be activated, which allows visualization of the procedure from within the inflatable member. If the visualization system is turned on before the inflatable system is inflated, the visualization system will show the inflatable member in a collapsed, delivery configuration and blood proximate the inflatable member. The user interface shown in FIG. 3 includes a Group control section which includes a Vision section on the left side that includes an Illumination interface, which allows a user to modify the intensity of light coming from the one or more light sources. There is another interface to turn the visualization system on and off.

Inflation/irrigation fluid can then be pumped from an inflation fluid source, through a shaft of the energy delivery device, and into the inflatable member, causing the inflatable member to inflate and assume an inflated configuration. The user interface in FIG. 3 shows an irrigation section of the left hand side, which includes a user interface element that allows the flow rate to be selected.

Once inflated, the energy delivery device can then be advanced as appropriate to make contact with target tissue. For example, in an ablation procedure in a left atrium, the energy delivery device can be advanced to make contact with atrial tissue that is near an ostium of a pulmonary vein. This causes the electrodes that are carried by the inflatable member to be urged against tissue.

The visualization system provides images in the field of view of the one or more optic components. The one or more optic components can include, for example, fiber optics, endoscopes, lenses, camera sensors, any of which can be disposed within the inflatable member. In the embodiment of the user interface shown in FIG. 3, there are 4 optic components, generating four images in the respective field of view. The system is adapted to overlay the images to create a 360 degree view from within the inflation member. The fields of view include, without limitation, the inflation/irrigation fluid (transparent), the inflation member, flex and flex circuits carried by the inflatable member. The general configuration of the electrodes can also be seen, even if the electrode material is not (e.g., if there is a light absorber between the electrode material and the optic component. Visualization system 108 in the user interface in FIG. 3 illustrates the exemplary overlapping of four images 126 obtained from four optic components, to create a 360 degree video image (which could also be still rather than video) around a longitudinal axis of the energy delivery device.

Figure 4:
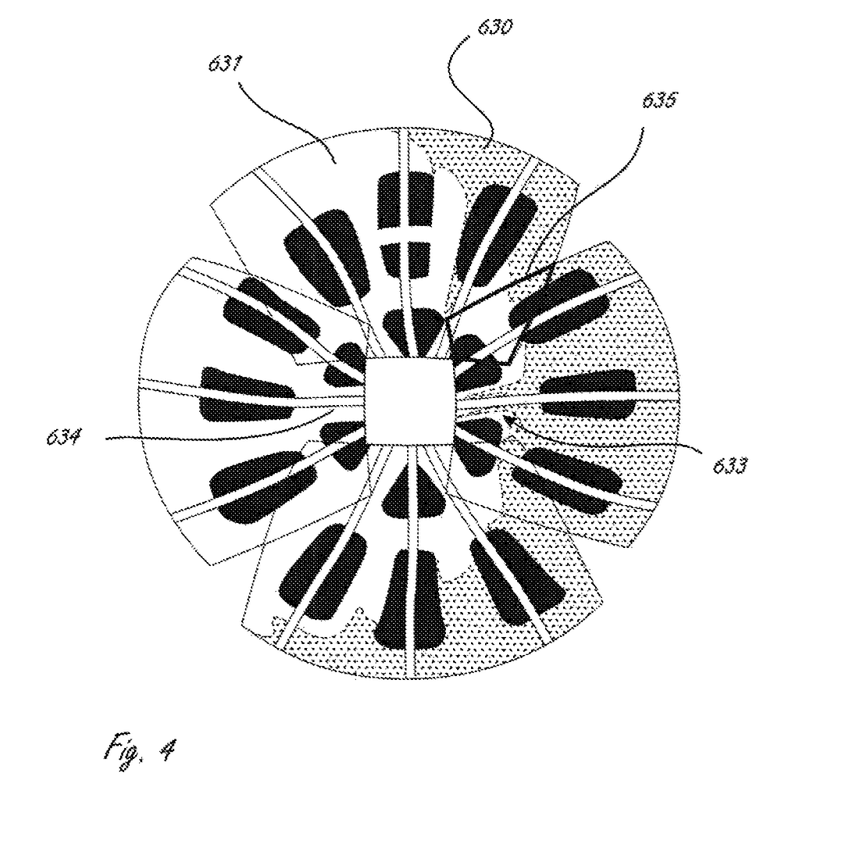
FIG. 4 is an exemplary image that can be presented in some of the user interfaces herein.

FIG. 4 illustrates exemplary imagery provided by the visualization system illustrating a visually identifiable optical difference between regions of the energy delivery device that are in contact with tissue, and those that are not. In the image of FIG. 4, white region 631 indicates where the energy delivery device is contacting the tissue, displacing blood from the field of view, and appears white (or at least different than the dotted pattern indicating red color of the blood) in the image. A white region indicates a lack of blood and or blood flow, and thus indicates that the energy delivery device is making contact with the tissue. A dotted pattern in the images indicates the presence of blood, and thus a lack of contact between the energy delivery device and the tissue.

For the exemplary applications herein, it is desirable to deliver energy to ablate tissue proximate a particular electrode if the electrode is in contact with tissue, and not surrounded by blood. Energizing an electrode surrounded by blood and not tissue can cause coagulation of the blood and ablates minimally or not at all. If the layer of blood is thin and therefore more transparent, energy may be delivered to adjacent electrodes, causing a less extensive ablation. It is thus desirable to send ablative energy to electrodes that, in the image of FIG. 4, are adjacent the white areas 631 (or at least the areas 631 that visually indicate a lack of blood, even if they are presented in a non-white manner). It is thus undesirable to deliver ablative energy to electrodes that are adjacent to area indicating blood flow 630. The visualization section 108 on the user interface in FIG. 3 can thus be used to visually determine which electrodes are in contact with the tissue and which are not. The determination can be performed manually, when user visualizes the image and makes a subjective determination. The determination can also be performed by software, such as software that can, in response to receiving the images or data indicative of the images, assess the optical differences in the different regions, and determine which electrodes are adjacent to portions of the energy delivery device in contact with tissue.

Exemplary ablation procedures will now be described. In this exemplary use, the energy delivery device is used to ablate a region of tissue surrounding or at an ostium of a pulmonary vein. A user can visually assess which electrodes are adjacent white regions on the image, and select those electrodes for being part of the energy delivery procedure. A user can additionally visually assess which electrodes are not making sufficient contact with tissue, and can choose not to deliver energy to those electrodes, such that they are not part of the energy delivery procedure.

In this embodiment of use, as much tissue as possible is surrounding and ostia is ablated during a single energy delivery process (i.e., during the "duration" set for the procedure). That is, it is intended to ablate as much tissue as possible at all once, rather than performing the procedure by activating electrodes sequentially and thus ablating tissue sequentially. This can dramatically cut down on the time needed to carry out the ablation procedure. A determination can first be made about which electrodes are going to participate, or be activated, during the ablation procedure, and which are not. Electrodes not selected for activation are referred to herein as inactive. Electrodes that are selected for activation are considered active. When it is not possible to create an ablation that completely surrounds the ostia and thereby isolates aberrant electrical signals, the energy delivery device may be manipulated to better contact the tissue previously not contacted and the ablation procedure repeated.

One exemplary use attempts to create energy densities at each active electrode that are equivalent, or as equivalent as possible. This helps create as uniform a lesion as possible between the active electrodes. One way to accomplish this is to select some of the active electrodes as energy "sources," and to select some of the active electrodes as energy "sinks." To do this, the system is adapted to allow the user to select some of the graphical elements 114 on the user interface to have an active source visual indicator that indicates that that particular electrode will be treated by the system as an active source. The system is further adapted to allow the user to select some of the graphical elements 114 on the user interface to have an active sink visual indicator, which indicates to the system that that particular electrode will be treated by the system as an active sink. In this embodiment, the system thus includes software that allows the user to toggle (via some user event) graphical elements between, at least, an optional selected state, an inactive state, an active source state, and an active sink state. Each of the different states has a unique visual indicator. For example, each of the three visual indicators can be a unique color or color combination. The state of the visual indicator establishes within the system which electrodes will be inactive, which will be active sources, and which will be active sinks.

The system can also be adapted to operate in monopolar mode, where all active electrodes are selected as source electrodes in the interface, and the sink electrode is the external return pad electrode. If all active electrodes are selected to be active sources, the system works in monopolar mode.

Figure 5:
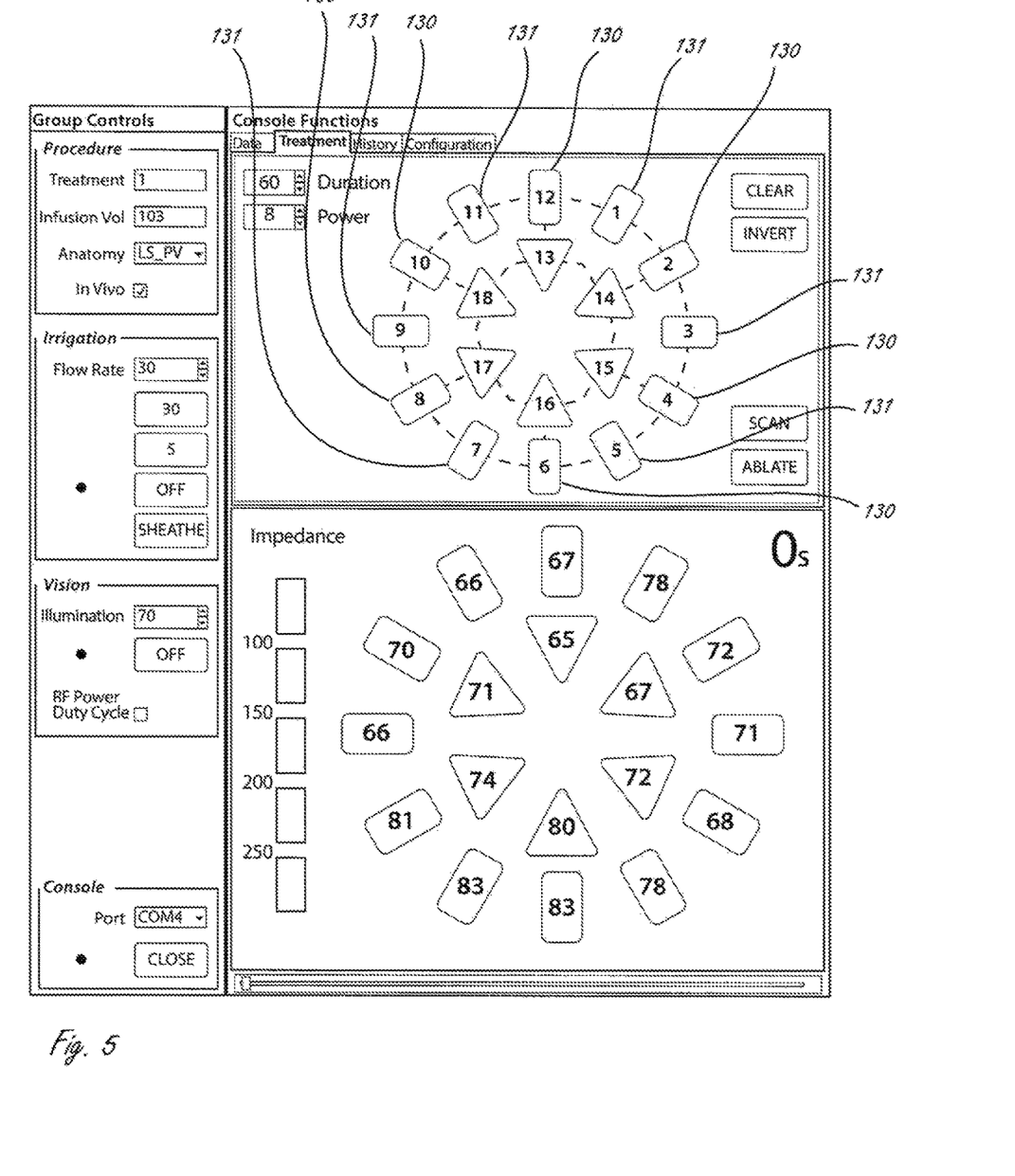
FIG. 5 is a portion of an exemplary user interface.

FIG. 5 illustrates a merely exemplary interface illustrating a plurality of graphical elements 130 that were selected to have an active source visual indicator (e.g., by pushing on or selecting the graphical element until it has a particular color indicative of being an active source), a plurality of graphical elements 131 that were selected to have an active sink visual indicator (e.g., by pushing on the graphical element until it has a particular color indicative of being an active sink), and a plurality of graphical elements (the inner ring electrodes marked 13 through 18) that were selected to be inactive, but which are not labeled in FIG. 5 for clarity. As a mere example, graphical elements that are selected by the user to be grey on the interface will be established by the system as inactive electrodes, graphical elements that are selected to be orange will be established by the system as active source electrodes, and graphical elements that are selected to be blue will be established by the system as active sink electrodes, graphical elements that are being addressed are half grey and half orange. Any other set of unique visual indicators may also be used.

The plurality of active source electrodes together create a first pole in a bipolar mode of the ablation device, and the plurality of active sink electrodes together create a second pole in the bipolar mode. The set of sink electrodes are electrically connected to a ground, and the set of source electrodes are connected to a source of energy. The system is adapted to apply the same current at the same frequency to each of the plurality of active source electrodes.

The user can also individually set the power level and duration using power interface 112 for each source electrode. That is, the system is adapted such that each source electrode can have its own power and duration set in the user interface.

Once the user has selected each of the electrodes to be inactive, active source, or active sink, the user can begin the energy delivery at the set power and duration (which can vary for the source electrodes) by pushing the "ablate" interface button in section 102.

Once the ablation procedure has begun, the system calculates impedance at each of the electrodes. The user interface in FIG. 3 includes impedance history section 106. Section 106 includes, for each active electrode, a chart 124 showing the history of calculated impedance 124 for that particular electrode. Each chart 124 is identified with the electrode number 120 for easy identification. The chart 124 presents the relative change in impedance for each electrode. The chart shows the current impedance as a percentage of the original impedance.

Impedance history section 106 provides the user the ability to visually monitor the history and the rate of change of the calculated impedance at each electrode. The rate of change of calculated impedance may be able to provide a good indication of where sufficient ablation has occurred. Impedance histories that show a quickly decreasing impedance likely indicate where the most effective ablation is occurring. The impedance changes for each electrode are due to the changes in the tissue that occur as it heats up and/or coagulates in response to the energy passing through it. Impedance drops as it heats up. The system is also adapted to visually indicate, for each impedance history chart, when the impedance drops below a preset threshold level. For example, once the impedance drops below this threshold value, the impedance can be presented on the graph in a different color (e.g., change from yellow to red). The overall shape of the impedance history can also generally indicate where desired ablation has taken place. For example, histories that show a relatively quick drop in relative impedance, followed by a general flattening out over a period of time (see electrodes "15," "16," and "17" in FIG. 3) indicate good ablation.

The user interface in FIG. 3, in section 104 (below section 102), each electrode has thereon a visual indicator 118 of the current impedance value, which is presented visually as a number. This section of the user interface also includes a color-coded categorization 116 that can be used to generally group each of the electrodes into one of a plurality of preset groupings of current impedance values. Each group can be visually distinguishable from the other (e.g., different colors) to provide a general indicator of the current impedance value for any particular electrode.

The user can use the impedance histories and/or the current impedance value to make a determination about the sufficiency of the ablation adjacent the one or more electrodes. For example, in this exemplary use (in which electrodes 7, 13, 14, and 18 were designated as inactive, and thus do not have an impedance history presented in section 106 of the interface), electrodes 1, 2, 8-12, and 15-17 showed good drops in impedance, and while observable in the figures, their impedance graphs changed from yellow to red as they dropped below the preset threshold. Conversely, the impedance history shown for electrodes 3-6 does not reflect much of a drop in impedance. This can be due to, for example, inadequate contact between electrodes 3-6 and tissue. These regions can then be ablated after repointing the energy delivery device.

The user can choose to perform additional ablation procedures as desired if there is a determination that calculated impedances for certain tissue regions were not to a desired level. Any or all portions of the procedure can be repeated, including moving the device, to perform additional ablation procedures. For example, the procedure can be repeated until impedance values are at a desire level. Different electrodes can be activated in any subsequent procedures.

The voltage at the sinks is zero or close to zero, and thus impedances at the sink electrodes cannot be directly calculate using known measured voltage and current. To estimate the impedance at each sink electrode, the methods herein can calculate the average voltage over all of the source electrodes, and in some cases apply a known preset factor to take into account any current that may be leaking out of the circuit. Once the estimated average voltage are calculated, the impedance at each sink electrode can then be estimated using the measure current at each sink. The impedance is then shown on the user interface.

When the physician is determining which electrodes to activate, it is possible that an odd number of electrodes are chosen for activation. That means the number of source electrodes will not be the same as the number of sink electrodes, and there will be two sink electrodes that are adjacent to one another. During an ablation procedure that takes place based on the selection of sources and sinks, there may be a region near the adjacent sinks where the tissue is not ablated as well as desired. To compensate for this, the system is adapted with an "invert" actuator on the interface (see FIG. 5), which when actuated, the system will change the existing sinks to sources and the existing sources to sinks. Another ablation procedure can then be performed, which will then create an effective lesion in any deficient area. In such usage the total amount of power will be maintained near that which would have been delivered it the invert were not used. Hence, if the invert procedure is activated once one half the power will be delivered in each at the pre-invert setting and one half at the post invert setting. If the invert is repeated twice, one quarter of the power will be delivered at each the settings.

Figure 6:
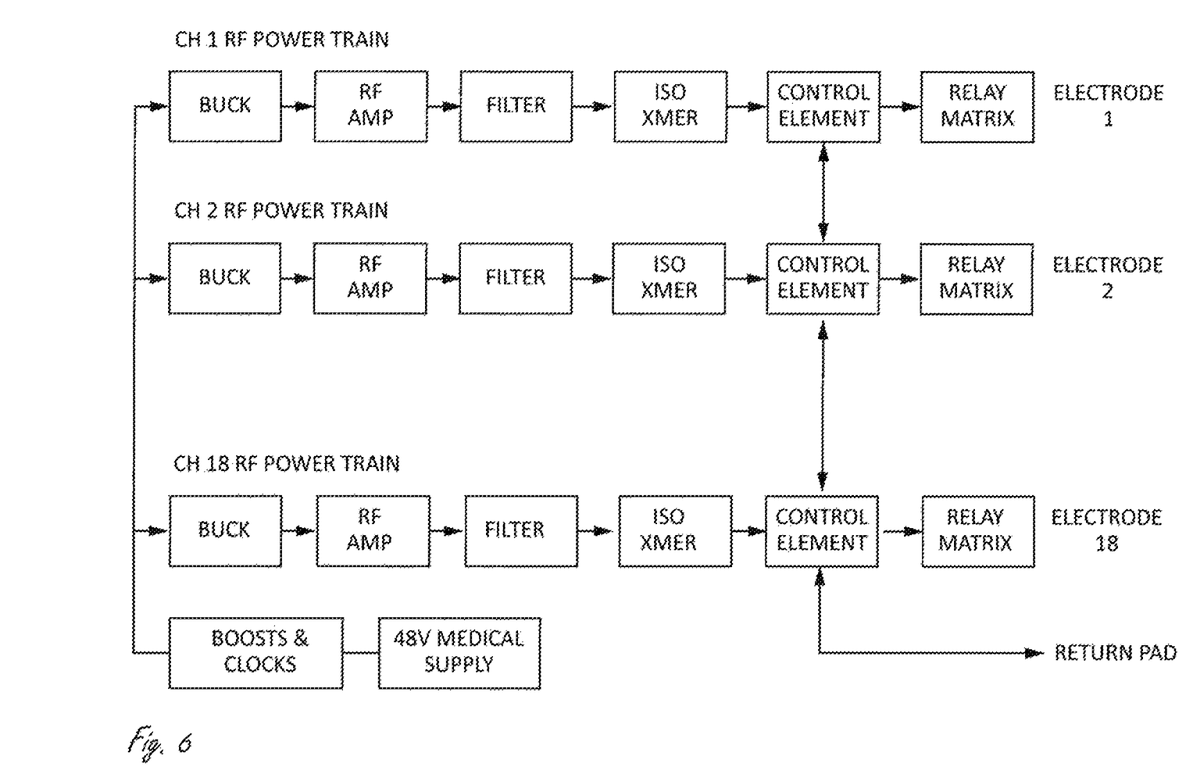
FIG. 6 is an exemplary schematic for an RF generator that can be used to delivery energy.

In some embodiments the generator, as set forth in FIG. 6, is constructed and adapted to, for each source electrode, maintain the power that was set at each source electrode using the interface. The control elements set forth in FIG. 6 communicate with each other (e.g., through a processing component) to adjust phase of each source electrode to ensure that all source electrodes are synchronous (i.e., in phase) at the ablation frequency. The control elements can also comprise voltage and current monitoring capabilities, which can be used to adjust voltage via each of the individual buck components to individually maintain the set power at each of the source electrodes during the ablation procedure. The system functionality applies to any of the embodiments herein, and can be generalized without reference to the specific system, including the catheter.

As set forth above, some of the electrodes are sources, and some are sinks (and some may be inactive). The energy density at each of the source electrodes can be controlled to be substantially equivalent. There may be some difference, however, between the energy density at the sinks which are not controlled. For example, the energy density at the sinks may vary by less than 20%, such as less than 10%, and still fall within the scope of the disclosure.

During the ablation procedure, the energy delivery to the tissue can cause undesired desiccation of the tissue. If desiccated, the impedance of the tissue abruptly and significantly rises. This can be monitored by the systems herein by calculating impedance. The systems can be adapted to immediately shut down energy delivery to any and all electrodes at which an abrupt and significant rise in impedance is calculated. The threshold can be established using the rate of impedance change and/or current impedance value calculated. The threshold may be established with reference to an absolute measurement of impedance or a relative measure of impedance such as a percentage of an initial impedance. For example, the system can have a max threshold, and if the impedance reaches that threshold, the system can be adapted to stop energy delivery (automatically or user-controlled). The system can also be adapted to have a minimum threshold (which can be relative) for impedance, and if the impedance reaches the minimum impedance, the system can similarly be adapted to stop energy to delivery to any electrode. Impedance may drop quickly to the threshold if, for example, the electrode is no longer making good contact with tissue, and is mostly contacting blood. The blood may be more conductive that the tissue, and hence the impedance drop. A quick dramatic drop in impedance can thus also be an indicator where an electrode may no longer be in good contact.

While not shown, a visual indicator appears on the impedance time histories (e.g., a red "X") to indicate visually that it has been energy has been stopped to that particular electrode, and also indicates at what time it was stopped. Additionally, in section 104, a visual indicator (e.g., a red "X") replaces the graphical element to visually indicate that energy to that particular electrode has stopped. Additionally, while not shown in FIG. 3, the graphical elements that are indicated to be inactive can be removed from bottom portion 104 (e.g., simply blackening them out, or not showing them at all). This can indicate visually in bottom portion 104 which electrodes are inactive.

Mapping of electrical activity of the tissue can also be performed with one or more ablation electrodes and/or mapping electrodes 419 on the energy delivery device. For example, the energy delivery device can be in electrical communication with standard ECG machines to monitor ECG activity of the tissue to determine if an electrical block has been formed.

It is understood that the user interface, and regions thereof, can be made the subject of a continuation design patent application. For example, the manner in which some or all of the sections are presented in the user interface in FIG. 3 can be the subject of a design application continuation. Any of the lines in the figures may be optional, and as such may be indicated as hashed lines in a design continuation application.

The invention claimed is:

1. A system for controlling an ablation procedure, comprising:

a user interface comprising a display; and a memory with a computer executable method stored thereon, the computer executable method adapted to cause to be displayed on the display a power interface and a plurality of graphical elements, each graphical element of the plurality of graphical elements representing a corresponding electrode carried by an ablation catheter in communication with an ablation energy generator, the computer executable method further adapted to, in response to user interaction with the display in a manner specific to one of the plurality of graphical elements, toggle the respective plurality of graphical elements between at least three visual indicators respectively representing an active source state having an active source visual indicator, an active sink state having an active sink visual indicator, and an inactive state with an inactive state visual indicator, wherein each of the three visual indicators are unique, wherein the active source state designates that the respective electrode is one of a plurality of active source electrodes, wherein the active sink state designates that the respective electrode is one of a plurality of active sink electrodes, wherein the plurality of active source electrodes together create a first pole in a bipolar mode, and wherein the plurality of active sink electrodes together create a second pole in the bipolar mode, wherein the system is adapted to connect the plurality of active sink electrodes to a ground, and to connect the plurality of active source electrodes to a source, wherein each active source electrode of the plurality of active source electrodes is adapted to be individually adjusted at a distinct power level using the power interface displayed on the display, wherein an energy density at each of the plurality of active sink electrodes is different from an energy density at each of the plurality of active source electrodes, wherein an energy density at each of the plurality of active sink electrodes is no more than 20% less than an energy density at each of the plurality of active source electrodes.

2. The system of claim 1 wherein the difference in energy densities is due to a difference in the number of active sink electrodes and the active source electrodes.

3. The system of claim 1, wherein the computer executable method is further adapted to, in response to user interaction with the display in a manner specific to one of the plurality of graphical elements, toggle the respective plurality of graphical elements between a selected state with a selected state visual indicator, wherein the selected state visual indicator is different than the active source visual indicator, the active sink visual indicator, and the inactive state visual indicator.

4. The system of claim 1, wherein the computer executable method is further adapted to calculate impedance associated with each of the active source electrodes and each of the active sink electrodes and tissue adjacent the respective source or sink based on a voltage and current delivered from the energy generator.

5. The system of claim 4, wherein the impedance at the sources is calculated in a first manner, and the impedance at the sinks is calculated in a second manner different than the first manner.

6. The system of claim 4, wherein the computer executable method is adapted to calculate the sink impedances as a percentage of the calculated source impedances.

7. A method of controlling an ablation procedure, comprising:

displaying on a user interface display a power interface and a plurality of graphical elements, each graphical element of the plurality of graphical elements representing a corresponding electrode carried by an ablation catheter in communication with an ablation energy generator;

in response to user interaction with the user interface display in a manner specific to one of the plurality of graphical elements, toggling the respective plurality of graphical elements between at least three visual indicators respectively representing an active source state having an active source visual indicator, an active sink state having an active sink visual indicator, and an inactive state with an inactive state visual indicator, wherein each of the three visual indicators are unique;

designating, via the user interface display, one or more of the electrodes with an active source state as one of a plurality of active source electrodes;

designating, via the user interface display, one or more of the electrodes with an active sink state as one of a plurality of active sink electrodes;

designating the plurality of active source electrodes together as a first pole in a bipolar mode, and designating the plurality of active sink electrodes together as a second pole in the bipolar mode; and in response to one or more of the designations, connecting the plurality of active sink electrodes to a ground and connecting the plurality of active source electrodes to a source;

wherein each active source electrode of the plurality of active source electrodes is adapted to be individually adjusted at a distinct power level using the power interface displayed on the display, wherein an energy density at each of the plurality of active sink electrodes is different from an energy density at each of the plurality of active source electrodes, wherein an energy density at each of the plurality of active sink electrodes is no more than 20% less than an energy density at each of the plurality of active source electrodes.

8. The method of claim 7, further comprising delivering ablation energy from the energy generator to the first pole.

9. The method of claim 7, further comprising stopping energy delivery to any electrode if a monitored change in impedance indicates an abrupt and significant change in calculated impedance.

10. The method of claim 7, further comprising stopping energy delivery to any electrode if a monitored impedance reaches a minimum threshold impedance or a maximum impedance threshold, which can occur automatically or via user input.

11. A system for monitoring an ablation procedure, comprising:

an ablation catheter including a plurality of ablation electrodes individually designable as being sources, sinks, or inactive;

an energy generator in communication with the ablation electrodes; and a memory with a computer executable method stored thereon, the computer executable method adapted to calculate impedance associated with each of the sources and each of the sinks and tissue adjacent the respective source or sink based on a voltage and current delivered from the energy generator; and a user interface comprising a display, the display including a plurality of impedance history regions, each one of the plurality of impedance history regions designated for one of the plurality of ablation electrodes;

wherein the system is adapted to display on each of the plurality of impedance history regions a line graph indicative of the respective calculated impedances over time for each of the selected plurality of ablation electrodes;

wherein each source electrode of the plurality of ablation electrodes is adapted to be individually adjusted at a distinct power level using a power interface displayed on the display;

wherein an energy density at each of a plurality of active sink electrodes is different from an energy density at each of a plurality of active source electrodes;

wherein an energy density at each of the plurality of active sink electrodes is no more than 20% less than an energy density at each of the plurality of active source electrodes.

12. The system of claim 11, wherein the computer executable method is adapted to calculate the sink impedances as a percentage of the calculated source impedances.

13. The system of claim 11, wherein the system is adapted to visually indicate on each of the plurality of impedance history regions if the respective impedance drops below a threshold impedance.

14. The system of claim 11, wherein the system is further adapted to cease energy delivery to any of the plurality of ablation electrodes if the impedance for any of the plurality of electrodes increases or decreases abruptly.

15. The system of claim 14, wherein the impedance at the sources is calculated in a first manner, and the impedance at the sinks is calculated in a second manner different than the first manner.

* * * * *